United States Patent
Yao et al.

(10) Patent No.: US 11,034,723 B2
(45) Date of Patent: Jun. 15, 2021

(54) HYBRID LIGAND, HYBRID BIOMIMETIC CHROMEDIA AND PREPARING METHOD AND USE THEREOF

(71) Applicant: ZHEJIANG UNIVERSITY, Zhejiang (CN)

(72) Inventors: Shanjing Yao, Zhejiang (CN); Dongqiang Lin, Zhejiang (CN); Qilei Zhang, Zhejiang (CN); Xujun Zou, Zhejiang (CN); Huili Lu, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 264 days.

(21) Appl. No.: 16/319,317

(22) PCT Filed: Jan. 16, 2018

(86) PCT No.: PCT/CN2018/072780
§ 371 (c)(1),
(2) Date: Jan. 18, 2019

(87) PCT Pub. No.: WO2019/127686
PCT Pub. Date: Jul. 4, 2019

(65) Prior Publication Data
US 2021/0009635 A1 Jan. 14, 2021

(30) Foreign Application Priority Data
Dec. 25, 2017 (CN) .......................... 201711419375.1

(51) Int. Cl.
C07K 1/22 (2006.01)
C07K 5/087 (2006.01)
C07K 16/00 (2006.01)
B01D 15/38 (2006.01)
B01J 20/26 (2006.01)
C07K 1/107 (2006.01)

(52) U.S. Cl.
CPC ........ C07K 5/0812 (2013.01); B01D 15/3809 (2013.01); B01D 15/3828 (2013.01); B01J 20/26 (2013.01); C07K 1/1077 (2013.01); C07K 1/22 (2013.01); C07K 16/00 (2013.01)

(58) Field of Classification Search
CPC .... B01D 15/361; B01D 15/363; B01D 15/38; B01D 15/3804; B01D 15/3809; B01D 15/3823; B01D 15/3828; B01D 15/3847; C07K 1/077; C07K 1/16; C07K 1/165; C07K 1/20; C07K 1/22; C07K 5/0812; C07K 16/00; B01J 20/22; B01J 20/262; B01J 20/64
See application file for complete search history.

(56) References Cited

U.S. PATENT DOCUMENTS

| | | | |
|---|---|---|---|
| 5,652,348 | A | 7/1997 | Burton et al. |
| 7,144,743 | B2 | 12/2006 | Boschetti et al. |
| 7,408,030 | B2 | 8/2008 | Carbonell et al. |

FOREIGN PATENT DOCUMENTS

| | | |
|---|---|---|
| CN | 101036877 | 9/2007 |
| CN | 101185881 | 5/2008 |
| CN | 101185882 | 5/2008 |
| CN | 103014880 | 4/2013 |
| CN | 104096544 | 10/2014 |
| CN | 104117345 | 10/2014 |
| CN | 104645949 | 5/2015 |

OTHER PUBLICATIONS

Niaik et al., "Performance of hexamer peptide ligands for affinity purification of immunoglobulin G from commercial cell culture media", Journal of Chromatography A, Dec. 4, 2010, pp. 1691-1700.
Zhao et al., "Octapeptide-based affinity chromatography of human immunoglobulin G: Comparisons of three different ligands", Journal of Chromatography A, Jul. 16, 2014, pp. 100-111.
Wang et al., "New tetrapeptide ligands designed for antibody purification with biomimetic chromatography: Molecular simulation and experimental validation", Biochemical Engineering Journal, Jul. 10, 2016, pp. 191-201.
Burton et al., "Hydrophobic charge induction chromatography: salt independent protein adsorption and facile elution with aqueous buffers", Journal of Chromatography A, Jul. 24, 1998, pp. 71-81.
Tong et al., "Multimodal charge-induction chromatography for antibody purification", Journal of Chromatography A, Dec. 21, 2015, pp. 258-264.
Lu et al., "Affinity biomimetic chromatography and its applications for antibody purification", CIESC Journal, Sep. 2016, pp. 3523-3535.
"International Search Report (Form PCT/ISA/210)", dated Sep. 19, 2018, pp. 1-4.

*Primary Examiner* — Jeffrey E. Russel
(74) *Attorney, Agent, or Firm* — JCIPRNET

(57) ABSTRACT

This invention relates to a hybrid ligand, a hybrid biomimetic chromedia and a preparing method and a use thereof, wherein the hybrid biomimetic chromedia takes hydrophilic porous microsphere as a substrate in chromatography, activated with allyl bromide and undergoing bromo-alcoholization with N-bromosuccinimide, then coupled with the hybrid ligands. The sequence of the hybrid ligand is phenylalanine-tyrosine-glutamine-5-aminobenzimidazole. The hybrid biomimetic chromedia has both of the two functional groups of phenylalanine-tyrosine-glutamine tripeptide and aminobenzimidazole, while maintaining the high antibody selectivity of polypeptide ligand, hydrophobic electric charge inductive ligand is introduced to achieve more moderate elution requirement, realizing effective antibody separation.

15 Claims, 4 Drawing Sheets

HYBRID LIGAND, HYBRID BIOMIMETIC CHROMEDIA AND PREPARING METHOD AND USE THEREOF

CROSS-REFERENCE TO RELATED APPLICATION

This application is a 371 of international application of PCT application serial no. PCT/CN2018/072780, filed on Jan. 16, 2018, which claims the priority benefit of China application no. 201711419375.1, filed on Dec. 25, 2017. The entirety of the above-mentioned international application of PCT application serial no. PCT/CN2018/072780 is hereby incorporated by reference herein and made a part of this specification.

BACKGROUND

Technical Field

This invention relates to the field of biomimetic chromatography, specifically relates to a hybrid ligand, a hybrid biomimetic chromedia, and a preparing method and a use thereof.

Related Art

Antibodies come in strong targeting and high biocompatibility, hence has great potential of being developed into drugs that treat diseases such as cancer. As antibody engineering keeps on developing, upstream antibody expression and preparation scale keep on improving. Therefore, development of efficient downstream separating and purifying technology is the key for antibody industry development.

Currently, protein A affinity chromatography is the mostly commonly used antibody capturing method, which has high selectivity. However, in protein A affinity chromatography, the medium comes in high price, the elution requirement is very strict, and the risk of ligand leakage exists. Therefore, it has become the hot spot in the industry to develop alternative technologies, and short chain polypeptide biomimetic chromatography and hydrophobic charge induction chromatography (HCIC) are two of the most important alternative technologies.

Short chain polypeptide biomimetic chromatography is a novel biomimetic affinity chromatography method taking short chain polypeptide compound as ligands, which is designed based on target proteins and has high selectivity, stability and good biocompatibility. U.S. Pat. No. 7,408,030 B2 discloses the hexapeptide ligand for separating antibody in feed liquid such as serum, ascitic fluid, cell culture fluid and milk. However, the arginine bearing electric charge in the ligand can absorb serum albumin, which reduces the selectivity of the ligand. Only at high salt concentration or when sodium caprylate is added can high purity IgG be obtained (J. Chromatogr. A, 1218:1691-1700, 2011). As Computer Molecular Simulateo (CMS) technology is introduced, the screening and optimum design of polypeptide ligand has been speeded up. Based on protein A affinity model, Chinese Patent CN 103014880 A discloses the octapeptide ligand, which shows good IgG separating performance. However, relevant mechanism research discovers that IgG binding is primarily dependent on static interaction, and NaCl needs to be added for elution (J. Chromatogr. A, 1359:100-111, 2014). Based on the molecular simulation of the Fc fragment binding sites of protein A, Chinese Patent CN 104645949 A discloses the tetrapeptide ligand, which has high IgG absorption capacity and salt resistance and moderate elution requirement. However, this ligand also has electrified arginine. It also has high serum albumin absorption quantity at pH>4, which affects the medium selectivity of IgG (Biochem. Eng. J., 114:191-201, 2016). Therefore, polypeptide ligand needs further optimized design to not only maintain good IgG binding selectivity, but also provide moderate elution requirement.

HCIC was proposed by Burton and Harding (J. Chromatogr. A, 814:71-81, 1998). Ligands in HCIC have both hydrophobic and ionizing groups, which, at neutral pH, bind protein through hydrophobic effect, and static repulsion effect between protein and the ligand is achieved by adjusting the pH of the solution, hence realizing elution. U.S. Pat. No. 5,652,348 B2 and U.S. Pat. No. 7,144,743 B2 describe methods for preparing HCIC medium, pointing out that effective protein binding can be realized at both low salt and high salt conditions. HCIC ligands reported already include indole compound (CN 101036877 A), imidazole compound (CN 101185882 A), compound composed of imidazole and benzene (CN 101185881 A), which have strong salt absorption resistance and moderate elution requirement. Chinese Patent CN 104096544 A reported a HCIC medium for antibody separation, which takes aminobenzimidazole as functional ligand and has high antibody binding performance and salt-independent absorption performance. However, HCIC ligand also has some shortcomings: mono ligand structure, antibody selectivity not high, huge amount of process optimization is required for antibodies of different sources, and it's difficult to separate and obtain high purity antibody from complex feed liquid.

Based on the above description, short chain polypeptide biomimetic chromatography and HCIC have their own advantages and disadvantages respectively. Chinese Patent CN 104117345 A proposes difunctional group medium composed of tryptophane and aminobenzimidazole, while maintaining the characteristics of aminobenzimidazole, with the introduction of tryptophane, antibody selectivity has been improved to a certain extent, though the improvement is limited, partial serum albumin absorption still occurs (J. Chromatogr. A, 1429:258-264, 2016).

SUMMARY

Proceeding from the inadequacy of the prior art, this invention is to provide a hybrid ligand, which has both of the two functional groups of phenylalanine-tyrosine-glutamine tripeptide and aminobenzimidazole, while maintaining the high antibody selectivity of polypeptide ligand, hydrophobic electric charge inductive ligand is introduced to achieve more moderate elution requirement, realizing effective antibody separation.

The technical solution provided by this invention is as follows.

A hybrid ligand, of which the structural formula is as follows:

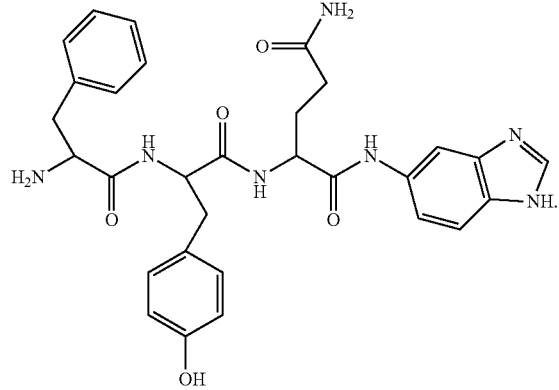 [SMILES: NC(=O)CCC(NC(=O)C(Cc1ccc(O)cc1)NC(=O)C(N)Cc1ccccc1)C(=O)Nc1ccc2[nH]cnc2c1]

The hybrid ligand in this invention comprises tripeptide and a heterocyclic small molecule, through computer molecule simulation, key residue at the binding site of protein A and antibody Fc was analyzed and evaluated to screen and design the tripeptide-heterocyclic small molecule hybrid ligand. The chemical synthesis method in the prior art can be adopted to synthesize tripeptide-heterocyclic small molecule, and the sequence is phenylalanine-tyrosine-glutamine-5-aminobenzimidazole.

This invention further provides a hybrid biomimetic chromedia, comprising a substrate in chromatography and a hybrid ligand, the said substrate in chromatography is hydrophilic porous microsphere with hydroxyl; the sequence of the said hybrid ligand is phenylalanine-tyrosine-glutamine-5-aminobenzimidazole;

the structural formula of the said hybrid ligand is as follows:

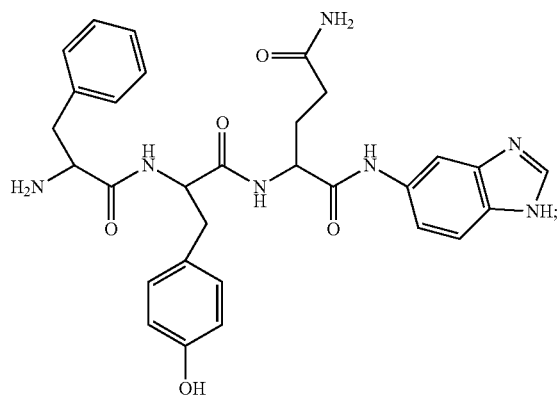 [SMILES: NC(=O)CCC(NC(=O)C(Cc1ccc(O)cc1)NC(=O)C(N)Cc1ccccc1)C(=O)Nc1ccc2[nH]cnc2c1]

the structural formula of the said hybrid biomimetic chromedia is as follows:

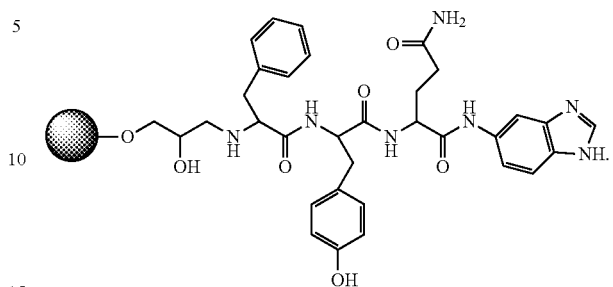

The structural formula of the hybrid biomimetic chromedia of this invention gives one hybrid ligand group as example only, the surface of the substrate in chromatography and the surface of the internal channel have huge amount of hybrid ligand groups.

The substrate in chromatography in this invention is hydrophilic microsphere with porous structure and surface hydroxyl, of which the structural formula is as follows:

the structural formula gives one —OH as example only, its surface has many —OHs.

In this invention, the hybrid biomimetic chromedia is obtained through coupling the hybrid ligand onto the substrate in chromatography, wherein the hybrid ligand has both of the two functional groups of phenylalanine-tyrosine-glutamine tripeptide and aminobenzimidazole, on one hand, the key residue of specific binding of protein A ligand and antibody Fc fragment is simulated by molecule simulation to optimize and design phenylalanine-tyrosine-glutamine tripeptide, so as to achieve high antibody selectivity of the ligand; on the other hand, hydrophobic electric charge inductive ligand-5-aminobenzimidazole is introduced to enhance hydrophobic effect, and through adjusting the pH of the solution, static repulsion effect is used to assist protein dissociation, reduce elution difficulty and improve elution requirement.

Preferably, the said substrate in chromatography is sepharose gel or cellulose microsphere.

This invention also provides a method for preparing the above-mentioned hybrid biomimetic chromedia, comprising the following steps:

1) performing an activating reaction by subjecting the substrate in chromatography with allyl bromide to obtain an activated substrate in chromatography;

wherein the reaction process in Step 1) is as follows:

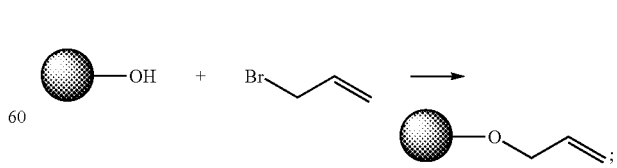

2) performing a bromo-alcoholization reaction by subjecting the activated substrate in chromatography with N-bromosuccinimide to obtain a bromo-alcoholized substrate;

wherein the reaction process in Step 2) is as follows:

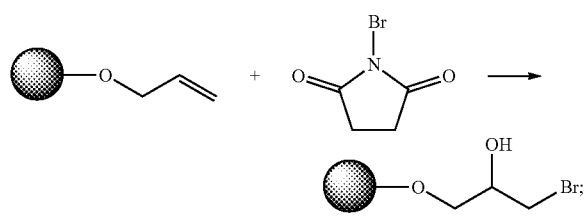

3) performing a coupled reaction by subjecting the bromo-alcoholized substrate and the hybrid ligand to obtain the hybrid biomimetic chromedia;
wherein the reaction process in Step 3) is as follows:

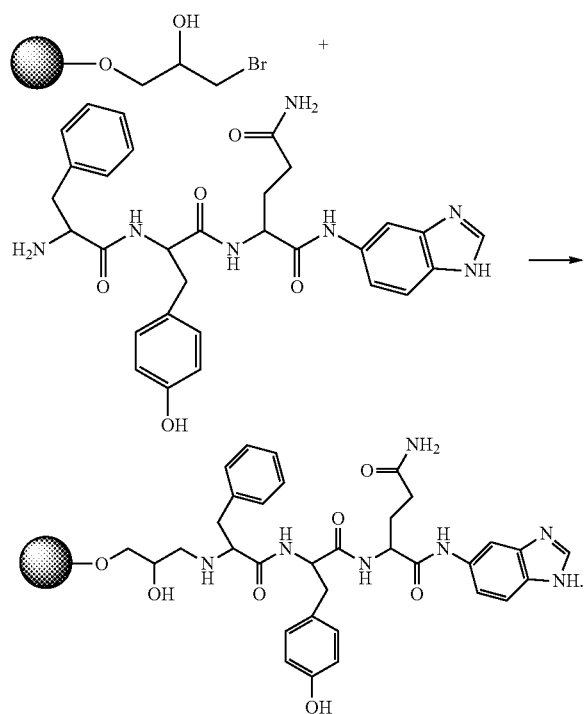

Preferably, the said activating reaction in Step 1) comprises: mixing the substrate in chromatography, a dimethyl sulfoxide solution, allyl bromide and sodium hydroxide, and conducting water bath reaction in the shaker, leaching and washing to obtain the activated substrate in chromatography.

Further preferably, the activating reaction in Step 1) comprises: after draining the substrate in chromatography, adding dimethyl sulfoxide solution of 18-22% (v/v) at 0.5-1.5 times of the mass of the substrate in chromatography, allyl bromide at 0.1-1.0 times of the mass of the substrate in chromatography, and sodium hydroxide at 0.1-0.5 times of the mass of the substrate in chromatography, conducting water bath at 28-32° C., conducting a reaction in shaker at 140-160 rpm rotation speed for 24-48 hours, leaching and washing with deionized water to obtain the activated substrate in chromatography.

Preferably, the said bromo-alcoholization reaction in Step 2) comprises: mixing the activated substrate in chromatography, acetone and N-bromosuccinimide, and conducting water bath reaction in the shaker, leaching and washing to obtain the bromo-alcoholized substrate.

Further preferably, the said bromo-alcoholization reaction in Step 2) comprises: taking the activated substrate in chromatography, adding acetone of 45-55% (v/v) at 1.0-3.0 times of the mass of the activated substrate in chromatography and N-bromosuccinimide at 0.1-0.3 times of the mass of the activated substrate in chromatography, conducting water bath at 28-32° C., conducting a reaction in shaker at 140-160 rpm rotation speed for 1-3 hours, leaching and washing with deionized water to obtain the bromo-alcoholized substrate.

Preferably, the said coupled reaction in Step 3) comprises: dissolving the bromo-alcoholized substrate and the hybrid ligand into dimethyl sulfoxide, adding sodium carbonate buffer for mixing, and then conducting water bath reaction in the shaker, leaching and washing to obtain hybrid biomimetic chromedia; the mass ratio of the said bromo-alcoholized substrate to the hybrid ligand is 1:0.1-0.3.

Further preferably, the said coupled reaction in Step 3) comprises: taking the bromo-alcoholized substrate into the reactor, weighing and taking phenylalanine-tyrosine-glutamine-5-aminobenzimidazole hybrid ligand at 0.1-0.3 times of the mass of the bromo-alcoholized substrate to dissolve in dimethyl sulfoxide at 0.5-1.0 times of the mass of the bromo-alcoholized substrate, then after mixing with sodium carbonate buffer of 0.8-1.2M at 1.0-3.0 times of the mass of the bromo-alcoholized substrate, taking the resulted mixture into the reactor, conducting water bath at 28-32° C., conducting a reaction in shaker at 140-160 rpm rotation speed for 8-12 hours, leaching, and repeatedly leaching and flushing with ionized water, 0.08-0.12M HCl and 0.08-0.12M NaOH to obtain the hybrid biomimetic chromedia.

Preferably, the said hybrid biomimetic chromedia in Step 3) continues to undergo a blocking reaction with an ethanolamine solution.

Preferably, the said blocking reaction comprises: adding the hybrid biomimetic chromedia into the ethanolamine solution to have a pH value of 8.0, and conducting water bath reaction in the shaker.

Further preferably, the said blocking reaction comprises: adding the hybrid biomimetic chromedia into the ethanolamine solution of 0.8-1.2 M (pH 8.0) at 1.0-5.0 times of the mass of the hybrid biomimetic chromedia, conducting water bath at 20-30° C., conducting a reaction in shaker at 140-160 rpm rotation speed for 4-8 hours, washing with deionized water and storing in ethanol solution of 18-22% (v/v).

This invention further provides a use of the above-mentioned hybrid biomimetic chromedia for separating antibody.

Comparing to the prior art, the benefits of this invention are as follow.

(1) In this invention, the density of the hybrid ligand is controllable, by adjusting the mass ratio of the bromo-alcoholized substrate to the hybrid ligand, medium of different ligand densities up to 70 μmol/g medium may be prepared.

(2) The hybrid biomimetic chromedia of this invention has high antibody affinity and high absorption quantity with static absorption capacity up to 80 mg/g medium or above and dynamic loading capacity up to 20 mg/ml medium or above.

(3) The hybrid biomimetic chromedia of this invention has strong antibody selectivity and very low serum albumin absorption quantity.

(4) The hybrid biomimetic chromedia of this invention has moderate elution requirement, when the pH is adjusted to 4.0-5.0, with the static repulsion effect between ligand and protein, efficient protein elution can be realized, avoiding adverse effect to the antibody structure and activity due to too acidic pH.

(5) The hybrid biomimetic chromedia of this invention comes in stable performance, is easy to wash and regenerate, and allows for over 100 times of repeated use.

To make the above features and advantages of the disclosure more comprehensible, several embodiments accompanied with drawings are described in detail as follows.

DETAILED DESCRIPTION OF DISCLOSED EMBODIMENTS

Below is further description of this invention in combination with specific embodiments.

Embodiment 1

Preparing Hybrid Ligand

Through computer molecule simulation, key residue at the binding site of protein A and antibody Fc was analyzed and evaluated to screen and design the tripeptide-heterocyclic small molecule hybrid ligand. The sequence of the hybrid ligand is phenylalanine-tyrosine-glutamine-5-aminobenzimidazole.

The hybrid ligand, of which the structural formula is as follows:

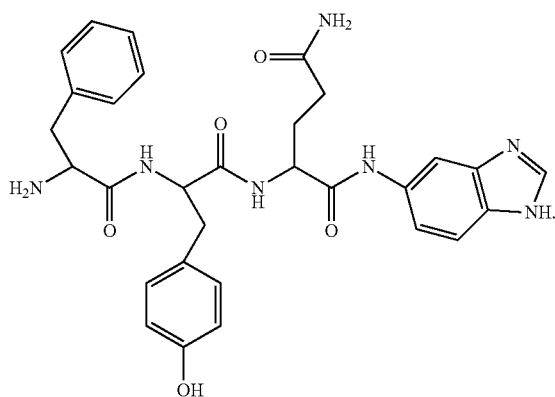 [SMILES: NC(=O)CCC(NC(=O)C(Cc1ccc(O)cc1)NC(=O)C(N)Cc1ccccc1)C(=O)Nc1ccc2[nH]cnc2c1]

The chemical synthesis method in the prior art may be adopted to synthesize the hybrid ligand, and the hybrid ligand in this embodiment is prepared by Chinese Peptide Co., Ltd.

Figure 1:
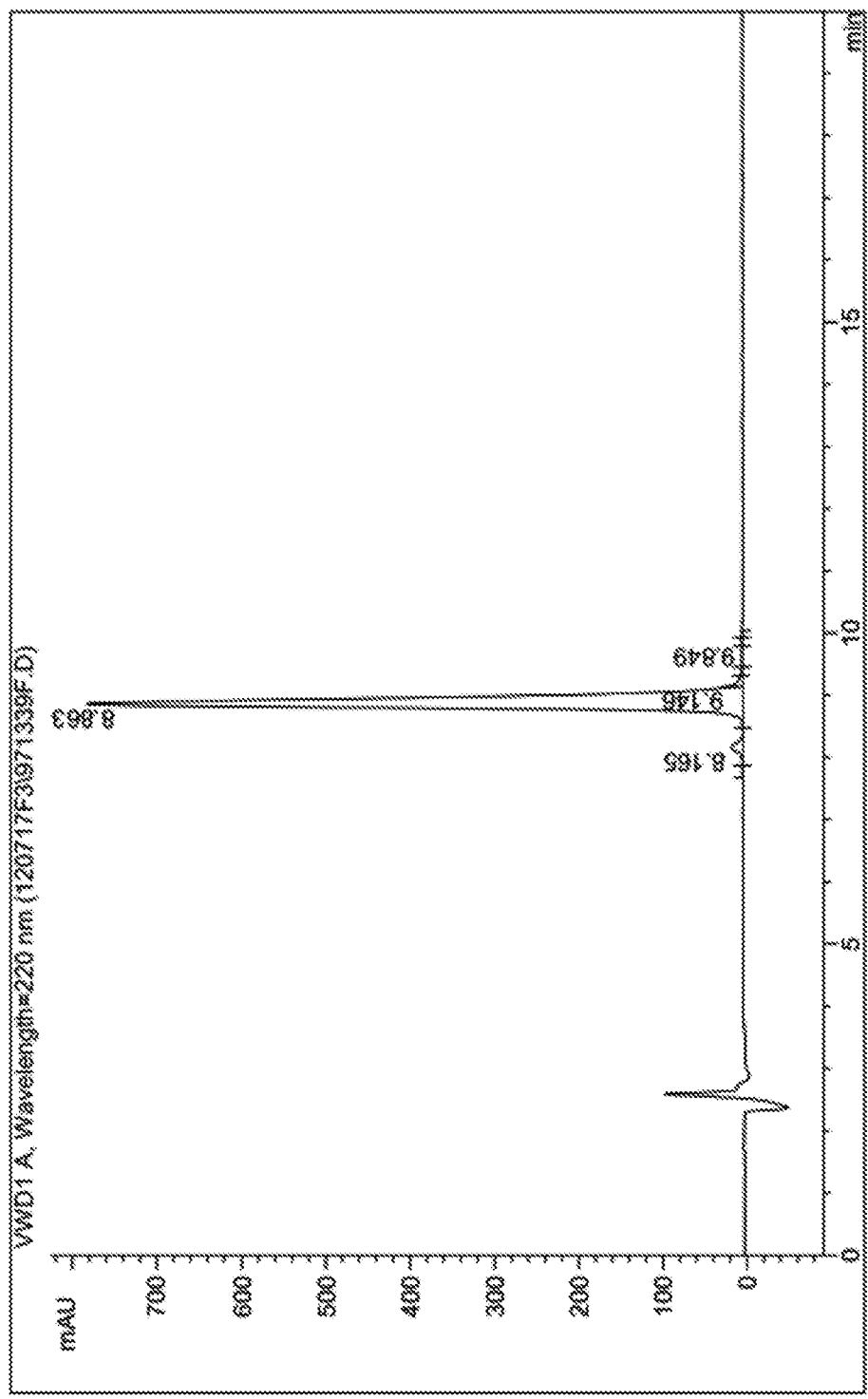
FIG. 1 is the high performance liquid chromatography of the hybrid ligand in embodiment 1.
Figure 2:
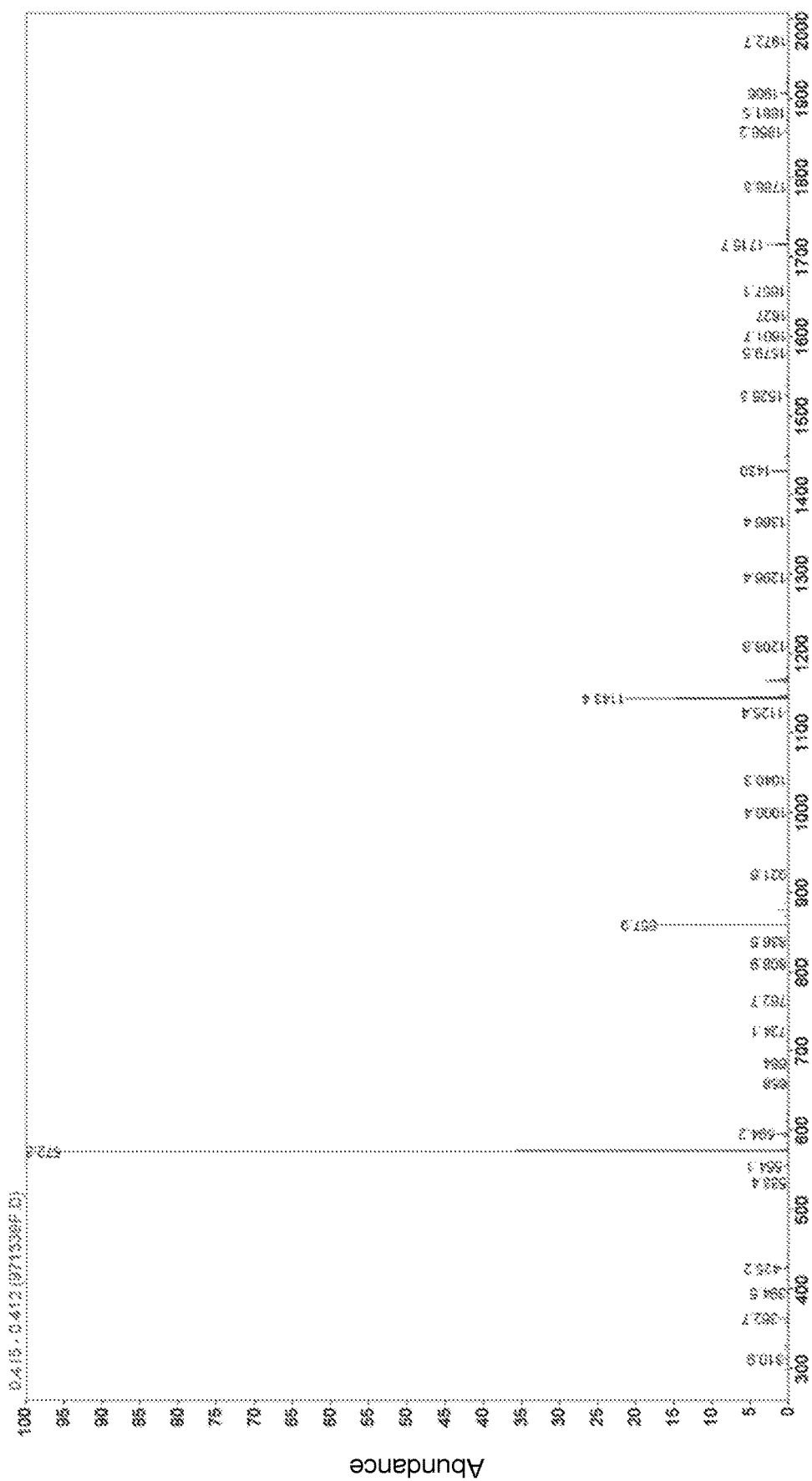
FIG. 2 is the mass spectrum of the hybrid ligand in embodiment 1.

High performance liquid chromatography and mass spectrum representation of the hybrid ligand in embodiment 1 is performed and is respectively as shown in FIG. 1 and FIG. 2.

Embodiment 2

Preparing Hybrid Biomimetic Chromedia

Take 3.0 g drained sepharose gel, add 3.0 g dimethyl sulfoxide of 20% (v/v), 1.5 g allyl bromide and 0.6 g sodium hydroxide, conduct an activating reaction in a shaker at 30° C. at 150 rpm for 24 hours, leach, wash with deionized water to obtain an activated substrate in chromatography.

Mix the activated substrate in chromatography, 6.0 g acetone of 50% (v/v) and 0.9 g N-bromosuccinimide to conduct a bromo-alcoholization reaction in a shaker at 30° C. at 150 rpm for 3 hours, leach, wash with deionized water to obtain a bromo-alcoholized substrate.

Mix 1.5 g dimethyl sulfoxide with 3.0 g sodium carbonate buffer of 1M, add 0.3 g phenylalanine-tyrosine-glutamine-5-aminobenzimidazole ligand to dissolve fully, then add the bromo-alcoholized substrate in chromatography, conduct a reaction in a shaker at 30° C. at 150 rpm for 12 hours, and repeatedly leach and flush with deionized water, 0.1M HCl and 0.1M NaOH to obtain a ligand coupled medium.

Finally, add the medium into 9.0 g ethanolamine solution of 1.0 M (pH 8.0), conduct a reaction in a shaker at 25° C. at 150 rpm for 4 hours, wash with deionized water to obtain a hybrid biomimetic chromedia.

Through analyzing by high performance liquid chromatography, the content of the left ligand in the bulk solution after reaction is 0.228 g, indicating that 0.072 g ligand is coupled onto the medium.

Through material balancing calculation, the medium ligand density is 42 μmol/g medium, and the saturated absorption capacity of human immunoglobulin is 85 mg/ml medium.

Embodiment 3

Preparing Hybrid Biomimetic Chromedia

Take 3.0 g drained sepharose gel, add 1.5 g dimethyl sulfoxide of 20% (v/v), 0.3 g allyl bromide and 0.3 g sodium hydroxide, conduct an activating reaction in a shaker at 30° C. at 150 rpm for 24 hours, leach, wash with deionized water to obtain an activated substrate in chromatography.

Mix the activated substrate in chromatography, 3.0 g acetone of 50% (v/v) and 0.3 g N-bromosuccinimide to conduct a bromo-alcoholization reaction in a shaker at 30° C. at 150 rpm for 1 hour, leach, wash with deionized water to obtain a bromo-alcoholized substrate.

Mix 1.5 g dimethyl sulfoxide with 3.0 g sodium carbonate buffer of 1M, add 0.3 g phenylalanine-tyrosine-glutamine-5-aminobenzimidazole ligand to dissolve fully, then add the bromo-alcoholized substrate in chromatography, conduct a reaction in a shaker at 30° C. at 150 rpm for 8 hours, and repeatedly leach and flush with deionized water, 0.1M HCl and 0.1M NaOH to obtain a ligand coupled medium.

Finally, add the medium into 3.0 g ethanolamine solution of 1.0 M (pH 8.0), conduct a reaction in a shaker at 25° C. at 150 rpm for 4 hours, wash with deionized water to obtain a hybrid biomimetic chromedia.

Through analyzing by high performance liquid chromatography, the content of the left ligand in the mother solution after reaction is 0.259 g, indicating that 0.041 g ligand is coupled onto the medium.

Embodiment 4

Preparing Hybrid Biomimetic Chromedia

Take 3.0 g drained sepharose gel, add 4.5 g dimethyl sulfoxide of 20% (v/v), 3 g allyl bromide and 1.5 g sodium hydroxide, conduct an activating reaction in a shaker at 30° C. at 150 rpm for 48 hours, leach, wash with deionized water to obtain an activated substrate in chromatography.

Mix the activated substrate in chromatography, 9.0 g acetone of 50% (v/v) and 0.9 g N-bromosuccinimide to conduct a bromo-alcoholization reaction in a shaker at 30° C. at 150 rpm for 3 hours, leach, wash with deionized water to obtain a bromo-alcoholized substrate.

Mix 3.0 g dimethyl sulfoxide with 6.0 g sodium carbonate buffer of 1M, add 0.9 g phenylalanine-tyrosine-glutamine-5-aminobenzimidazole ligand to dissolve fully, then add the bromo-alcoholized substrate in chromatography, conduct a reaction in a shaker at 30° C. at 150 rpm for 12 hours, and repeatedly leach and flush with deionized water, 0.1M HCl and 0.1M NaOH to obtain a ligand coupled medium.

Finally, add the medium into 15.0 g ethanolamine solution of 1.0 M (pH 8.0), conduct a reaction in a shaker at 25° C. at 150 rpm for 8 hours, wash with deionized water to obtain a hybrid biomimetic chromedia.

Through analyzing by high performance liquid chromatography, the content of the left ligand in the mother solution after reaction is 0.775 g, indicating that 0.125 g ligand is coupled onto the medium.

Through material balancing calculation, the medium ligand density is 73 μmol/g medium, and the saturated absorption capacity of human immunoglobulin is 92 mg/ml medium.

Embodiment 5

Preparing Hybrid Biomimetic Chromedia

Take 3.0 g drained sepharose gel, add 3.0 g dimethyl sulfoxide of 20% (v/v), 1.5 g allyl bromide and 0.9 g sodium hydroxide, conduct an activating reaction in a shaker at 30° C. at 150 rpm for 36 hours, leach, wash with deionized water to obtain an activated substrate in chromatography.

Mix the activated substrate in chromatography, 6.0 g acetone of 50% (v/v) and 0.6 g N-bromosuccinimide to conduct a bromo-alcoholization reaction in a shaker at 30° C. at 150 rpm for 2 hours, leach, wash with deionized water to obtain a bromo-alcoholized substrate.

Mix 2.0 g dimethyl sulfoxide with 6.0 g sodium carbonate buffer of 1M, add 0.9 g phenylalanine-tyrosine-glutamine-5-aminobenzimidazole ligand to dissolve fully, then add the bromo-alcoholized substrate in chromatography, conduct a reaction in a shaker at 30° C. at 150 rpm for 10 hours, and repeatedly leach and flush with deionized water, 0.1M HCl and 0.1M NaOH to obtain a ligand coupled medium.

Finally, add the medium into 9.0 g ethanolamine solution of 1.0 M (pH 8.0), conduct a reaction in a shaker at 25° C. at 150 rpm for 6 hours, wash with deionized water to obtain a hybrid biomimetic chromedia.

Through analyzing by high performance liquid chromatography, the content of the left ligand in the mother solution after reaction is 0.816 g, indicating that 0.084 g ligand is coupled onto the medium.

Through material balancing calculation, the medium ligand density is 49 μmol/g medium, and the saturated absorption capacity of human immunoglobulin is 88 mg/ml medium.

Embodiment 6

Preparing Hybrid Biomimetic Chromedia

Take 3.0 g drained sepharose gel, add 1.5 g dimethyl sulfoxide of 20% (v/v), 0.3 g allyl bromide and 1.5 g sodium hydroxide, conduct an activating reaction in a shaker at 30° C. at 150 rpm for 24 hours, leach, wash with deionized water to obtain an activated substrate in chromatography.

Mix the activated substrate in chromatography, 9.0 g acetone of 50% (v/v) and 0.9 g N-bromosuccinimide to conduct a bromo-alcoholization reaction in a shaker at 30° C. at 150 rpm for 1 hour, leach, wash with deionized water to obtain a bromo-alcoholized substrate.

Mix 1.5 g dimethyl sulfoxide with 9.0 g sodium carbonate buffer of 1M, add 0.3 g phenylalanine-tyrosine-glutamine-5-aminobenzimidazole ligand to dissolve fully, then add the bromo-alcoholized substrate in chromatography, conduct a reaction in a shaker at 30° C. at 150 rpm for 12 hours, and repeatedly leach and flush with deionized water, 0.1M HCl and 0.1M NaOH to obtain a ligand coupled medium.

Finally, add the medium into 9.0 g ethanolamine solution of 1.0 M (pH 8.0), conduct a reaction in shaker at 25° C. at 150 rpm for 4 hours, wash with deionized water to obtain a hybrid biomimetic chromedia.

Through analyzing by high performance liquid chromatography, the content of the left ligand in the mother solution after reaction is 0.254 g, indicating that 0.046 g ligand is coupled onto the medium.

Through material balancing calculation, the medium ligand density is 27 μmol/g medium, and the saturated absorption capacity of human immunoglobulin is 70 mg/ml medium.

Embodiment 7

Preparing Hybrid Biomimetic Chromedia

Take 3.0 g cellulose microsphere, add 3.0 g dimethyl sulfoxide of 20% (v/v), 1.5 g allyl bromide and 0.6 g sodium hydroxide, conduct an activating reaction in a shaker at 30° C. at 150 rpm for 24 hours, leach, wash with deionized water to obtain an activated substrate in chromatography.

Mix the activated substrate in chromatography, 6.0 g acetone of 50% (v/v) and 0.9 g N-bromosuccinimide to conduct a bromo-alcoholization reaction in a shaker at 30° C. at 150 rpm for 3 hours, leach, wash with deionized water to obtain a bromo-alcoholized substrate.

Mix 1.5 g dimethyl sulfoxide with 3.0 g sodium carbonate buffer of 1M, add 0.3 g phenylalanine-tyrosine-glutamine-5-aminobenzimidazole ligand to dissolve fully, then add the bromo-alcoholized substrate in chromatography, conduct a reaction in a shaker at 30° C. at 150 rpm for 12 hours, and repeatedly leach and flush with deionized water, 0.1M HCl and 0.1M NaOH to obtain a ligand coupled medium.

Finally, add the medium into 9.0 g ethanolamine solution of 1.0 M (pH 8.0), conduct a reaction in a shaker at 25° C. at 150 rpm for 4 hours, wash with deionized water to obtain a hybrid biomimetic chromedia.

Through analyzing by high performance liquid chromatography, the content of the left ligand in the mother solution after reaction is 0.232 g, indicating that 0.068 g ligand is coupled onto the medium.

Through material balancing calculation, the medium ligand density is 40 μmol/g medium, and the saturated absorption capacity of human immunoglobulin is 80 mg/ml medium.

Use Example 1

Take the chromedia obtained from embodiment 2 and fill 1 ml of the same into the Tricorn 5/100 chromatographic column, determine the protein breakthrough curve using ÄKTA explorer 100 chromatographic system.

Figure 3:
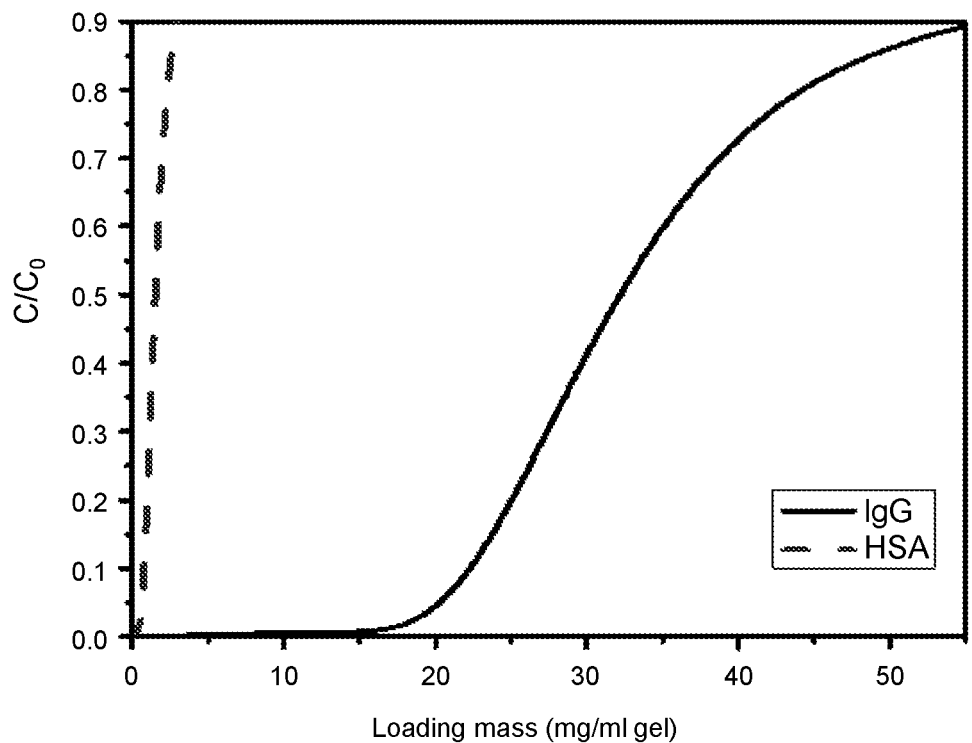
FIG. 3 is the breakthrough curve comparison diagram between human IgG and human serum albumin (HSA) in use example 1.

Respectively prepare 2 mg/ml human IgG solution and 2 mg/ml HSA solution as the loading sample liquid, and adjust pH to 7.0. Take 20 mM phosphate buffer (pH 7.0) as equilibration buffer to fully equilibrate the bed, feed sample at 0.5 ml/min flow rate until 90% protein breakthrough, detect the protein concentration of the effluent at the point of 280 nm with UV detector, the result is as shown in FIG. 3. Based on the loading sample volume at 10% protein breakthrough, calculate the dynamic loading capacity, IgG dynamic loading capacity is 22 mg/ml, HSA dynamic loading capacity is 0.8 mg/ml. Elute IgG with acetic acid-sodium acetate buffer at pH4.0 until the yield reaches 90%.

Use Example 2

Take the chromedia obtained from embodiment 2 and fill 1 ml of the same into the Tricorn 5/100 chromatographic column, determine the separating performance of the mixed protein using ÄKTA explorer 100 chromatographic system.

Figure 4:
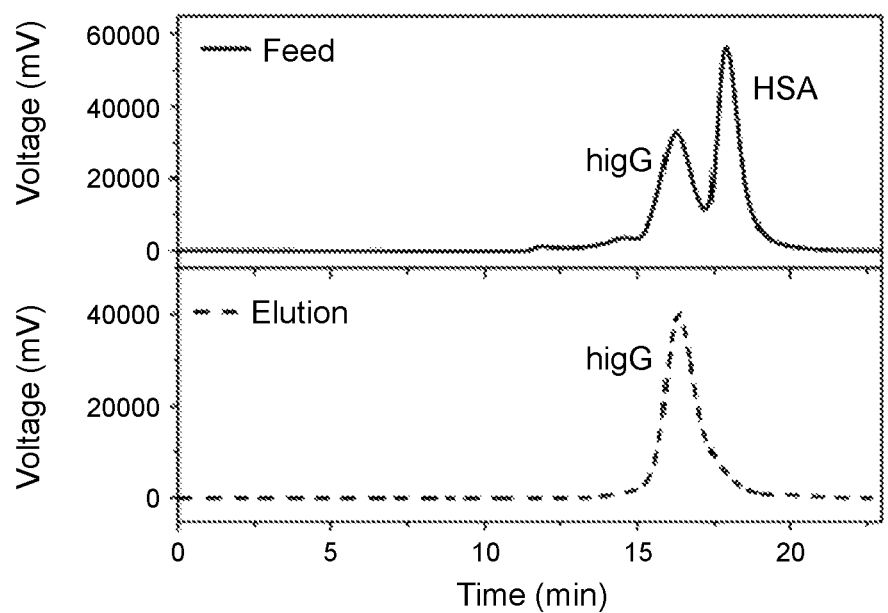
FIG. 4 is the high performance liquid chromatography of the mixed protein separation material and elution fractions in use example 2.

Prepare mixed protein solution containing 1 mg/ml human IgG and 4 mg/ml HSA as the loading sample liquid, and adjust pH to 7.0. Take 20 mM phosphate buffer (pH 7.0) as equilibration buffer to fully equilibrate the bed, feed 5 ml mixed protein solution sample at 0.5 ml/min flow rate, after sample loading is completed, flush with 20 mM phosphate buffer (pH 7.0) to the base line, then elute with 20 mM acetate buffer (pH 4.0), detect the protein concentration of the effluent at the point of 280 nm with UV detector, collect the elution fractions. Conduct HPLC analysis of the collected fractions, and the result is as shown in FIG. 4. Through calculation, IgG purity is 99.0%, the yield is 91.5%.

Use Example 3

Take the chromedia obtained from embodiment 7 and fill 1 ml of the same into the Tricorn 5/100 chromatographic column, determine the separating performance of the mixed protein using ÄKTA explorer 100 chromatographic system.

Figure 5:
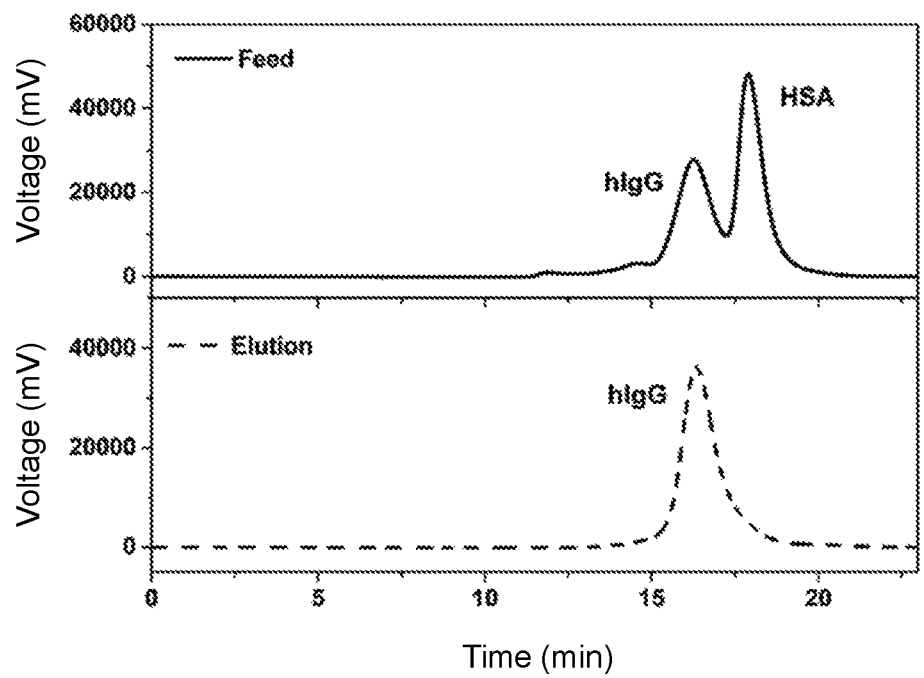
FIG. 5 is the high performance liquid chromatography of the mixed protein separation material and elution fractions in use example 3.

Prepare mixed protein solution containing 1 mg/ml human IgG and 4 mg/ml HSA as the loading sample liquid, and adjust pH to 7.0. Take 20 mM phosphate buffer (pH 7.0) as equilibration buffer to fully equilibrate the bed, feed 5 ml mixed protein solution sample at 0.5 ml/min flow rate, after sample loading is completed, flush with 20 mM phosphate buffer (pH 7.0) to the base line, then elute with 20 mM acetate buffer (pH 4.0), detect the protein concentration of the effluent at the point of 280 nm with UV detector, collect the elution fractions. Conduct HPLC analysis of the collected fractions, and the result is as shown in FIG. 5. Through calculation, IgG purity is 89.1%, the yield is 92.8%.

Use Example 4

Take the chromedia obtained from embodiment 2 and fill 1 ml of the same into the Tricorn 5/100 chromatographic column, determine the protein breakthrough curve using ÄKTA explorer 100 chromatographic system.

Figure 6:
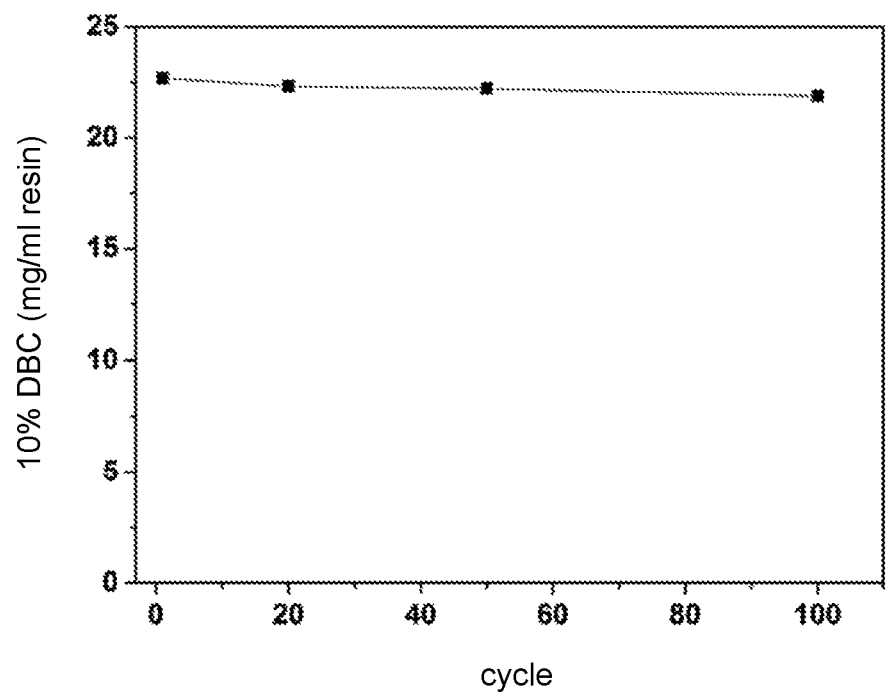
FIG. 6 is the dynamic loading capacity change diagram after using different cycles in use example 4.

Prepare 2 mg/ml human IgG solution as the loading sample liquid, and adjust pH to 7.0. Take 20 mM phosphate buffer (pH 7.0) as equilibration buffer to fully equilibrate the bed, feed sample at 0.5 ml/min flow rate until 90% protein breakthrough, detect the protein concentration of the effluent at the point of 280 nm with UV detector, based on the loading sample volume at 10% protein breakthrough, calculate the dynamic loading capacity at 10% breakthrough. After the medium goes through the loading sample-flush-elution-regeneration cycle for 20 times, 50 times and 100 times of use, repeat the above-described operation to measure IgG dynamic loading capacity. At 1, 20, 50 and 100 cycles of the medium, the IgG dynamic loading capacities are respectively 22.68 mg/ml medium, 22.31 mg/ml medium, 22.21 mg/ml medium and 21.89 mg/ml medium, after 100 cycles of use, the loading capacity decreased by 3.5% only, refer to FIG. 6 for specific change curve.

What is claimed is:
1. A hybrid ligand, wherein a structural formula of the hybrid ligand is as follows:

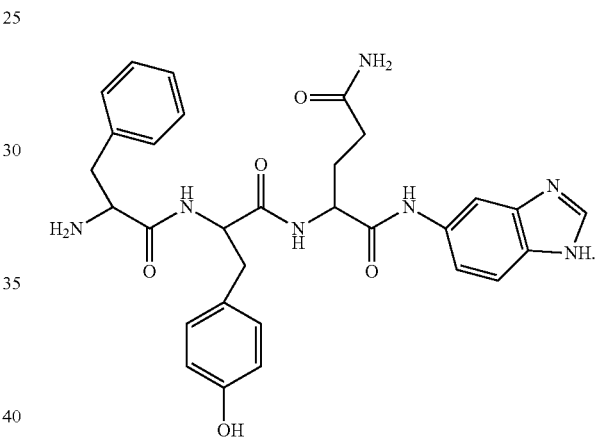

2. A hybrid biomimetic chromedia, comprising a substrate in chromatography and a hybrid ligand, wherein the substrate in chromatography is a hydrophilic porous microsphere comprising hydroxyl;
a structural formula of the hybrid ligand is as follows:

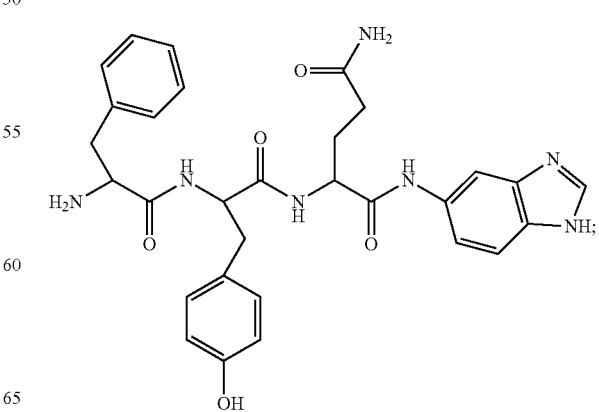

and
a structural formula of the hybrid biomimetic chromedia is as follows:

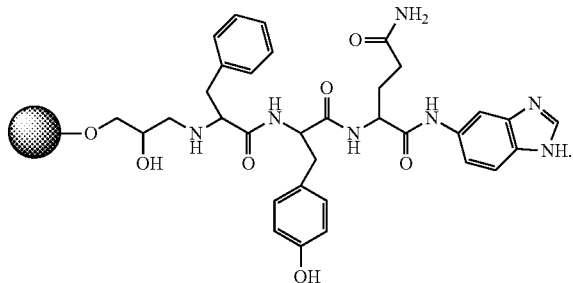 [SMILES: COCC(O)CNC(Cc1ccccc1)C(=O)NC(Cc1ccc(O)cc1)C(=O)NC(CCC(N)=O)C(=O)Nc1ccc2[nH]cnc2c1]

3. The hybrid biomimetic chromedia according to claim 2, wherein the substrate in chromatography is sepharose gel or cellulose microsphere.

4. A method for preparing the hybrid biomimetic chromedia according to claim 2, comprising the following steps:
  1) performing an activating reaction by subjecting the substrate in chromatography with allyl bromide to obtain an activated substrate in chromatography;
  2) performing a bromo-alcoholization reaction by subjecting the activated substrate in chromatography with N-bromosuccinimide to obtain a bromo-alcoholized substrate; and
  3) performing a coupled reaction by subjecting the bromo-alcoholized substrate and the hybrid ligand to obtain the hybrid biomimetic chromedia.

5. The method according to claim 4, wherein the activating reaction in Step 1) comprises: mixing the substrate in chromatography, a dimethyl sulfoxide solution, allyl bromide and sodium hydroxide, and conducting water bath reaction in a shaker, leaching and washing to obtain the activated substrate in chromatography.

6. The method according to claim 4, wherein the bromo-alcoholization reaction in Step 2) comprises: mixing the activated substrate in chromatography, acetone and N-bromosuccinimide, and conducting water bath reaction in a shaker, leaching and washing to obtain the bromo-alcoholized substrate.

7. The method according to claim 4, wherein the coupled reaction in Step 3) comprises: dissolving the bromo-alcoholized substrate and the hybrid ligand into dimethyl sulfoxide, adding sodium carbonate buffer for mixing, and then conducting water bath reaction in a shaker, leaching and washing to obtain the hybrid biomimetic chromedia; and a mass ratio of the bromo-alcoholized substrate to the hybrid ligand is 1:0.1-0.3.

8. The method according to claim 4, wherein the hybrid biomimetic chromedia in Step 3) continues to undergo a blocking reaction with an ethanolamine solution.

9. The method according to claim 8, wherein the blocking reaction comprises: adding the hybrid biomimetic chromedia into the ethanolamine solution to have a pH value of 8.0, and conducting water bath reaction in a shaker.

10. A method for preparing the hybrid biomimetic chromedia according to claim 3, comprising the following steps:
  1) performing an activating reaction by subjecting the substrate in chromatography with allyl bromide to obtain an activated substrate in chromatography;
  2) performing a bromo-alcoholization reaction by subjecting the activated substrate in chromatography with N-bromosuccinimide to obtain a bromo-alcoholized substrate; and
  3) performing a coupled reaction by subjecting the bromo-alcoholized substrate and the hybrid ligand to obtain the hybrid biomimetic chromedia.

11. The method according to claim 10, wherein the activating reaction in Step 1) comprises: mixing the substrate in chromatography, a dimethyl sulfoxide solution, allyl bromide and sodium hydroxide, and conducting water bath reaction in a shaker, leaching and washing to obtain the activated substrate in chromatography.

12. The method according to claim 10, wherein the bromo-alcoholization reaction in Step 2) comprises: mixing the activated substrate in chromatography, acetone and N-bromosuccinimide, and conducting water bath reaction in a shaker, leaching and washing to obtain the bromo-alcoholized substrate.

13. The method according to claim 10, wherein the coupled reaction in Step 3) comprises: dissolving the bromo-alcoholized substrate and the hybrid ligand into dimethyl sulfoxide, adding sodium carbonate buffer for mixing, and then conducting water bath reaction in a shaker, leaching and washing to obtain the hybrid biomimetic chromedia; and a mass ratio of the bromo-alcoholized substrate to the hybrid ligand is 1:0.1-0.3.

14. The method according to claim 10, wherein the hybrid biomimetic chromedia in Step 3) continues to undergo a blocking reaction with an ethanolamine solution.

15. The method according to claim 14, wherein the blocking reaction comprises: adding the hybrid biomimetic chromedia into the ethanolamine solution to have a pH value of 8.0, and conducting water bath reaction in a shaker.

* * * * *